United States Patent [19]
Ikonen

[11] Patent Number: 5,758,639
[45] Date of Patent: Jun. 2, 1998

[54] COMBINATION OF A HELMET AND A RESPIRATROR AND A METHOD FOR USING IT

[76] Inventor: Alpo Ikonen, FIN-40950, Murame, Finland

[21] Appl. No.: 782,733

[22] PCT Filed: Sep. 6, 1993

[86] PCT No.: PCT/FI93/00354

§ 371 Date: Apr. 26, 1995

§ 102(e) Date: Apr. 26, 1995

[87] PCT Pub. No.: WO94/05175

PCT Pub. Date: Mar. 17, 1994

Related U.S. Application Data

[63] Continuation of Ser. No. 397,127, Apr. 26, 1995, abandoned.

[30] Foreign Application Priority Data

Sep. 8, 1992 [FI] Finland .................................. 924020
Sep. 28, 1992 [FI] Finland .................................. 924345

[51] Int. Cl.$^6$ ...................................................... A62B 7/00
[52] U.S. Cl. ...................... 128/201.25; 128/206.12; 128/201.23; 128/201.14
[58] Field of Search ........................ 128/200.24, 201.15, 128/201.14, 201.25, 204.18, 205.12, 205.25, 205.29, 206.12, 206.27, 206.28, 206.21, 201.22, 20.23; 2/171.3, 173, 6

[56] References Cited

U.S. PATENT DOCUMENTS

| | | | |
|---|---|---|---|
| 2,377,122 | 5/1945 | Bakke | 128/201.25 |
| 3,910,269 | 10/1975 | Ansite et al. | 128/201.24 |
| 4,502,480 | 3/1985 | Yamamoto | 128/301.25 |
| 4,549,542 | 10/1985 | Chien | 128/201.24 |
| 4,667,348 | 5/1987 | Sundahl . | |
| 4,817,596 | 4/1989 | Gallet | 128/201.24 |
| 5,212,843 | 5/1993 | Kamata | 2/426 |
| 5,245,994 | 9/1993 | Chang et al. | 128/201.23 |

FOREIGN PATENT DOCUMENTS

| | | | |
|---|---|---|---|
| 0235373 | 9/1987 | European Pat. Off. . | |
| 325959 | 2/1989 | European Pat. Off. | 128/201.23 |
| 427117 | 2/1990 | European Pat. Off. | 2/410 |
| 2811620 | 9/1979 | Germany . | |
| 3332577 | 3/1985 | Germany . | |

Primary Examiner—Aaron J. Lewis
Assistant Examiner—William J. Deane, Jr.
Attorney, Agent, or Firm—Kane, Dalsimer, Sullivan, Kurucz, Levy, Eisele and Richard, LLP

[57] ABSTRACT

The invention relates to a combination of a helmet or a protective mask and a respirator that can function under ram pressure. The helmet's chin arch (1) contains a face element (4), a filter (3) and inhalation and exhalation valves (5,6). The air can, for instance, flow through the apertures (2) in the chin arch (1) to the respirator. The face element (4) can be moved by means of a lever (11) in accordance with the pressure caused by the air stream.

18 Claims, 7 Drawing Sheets

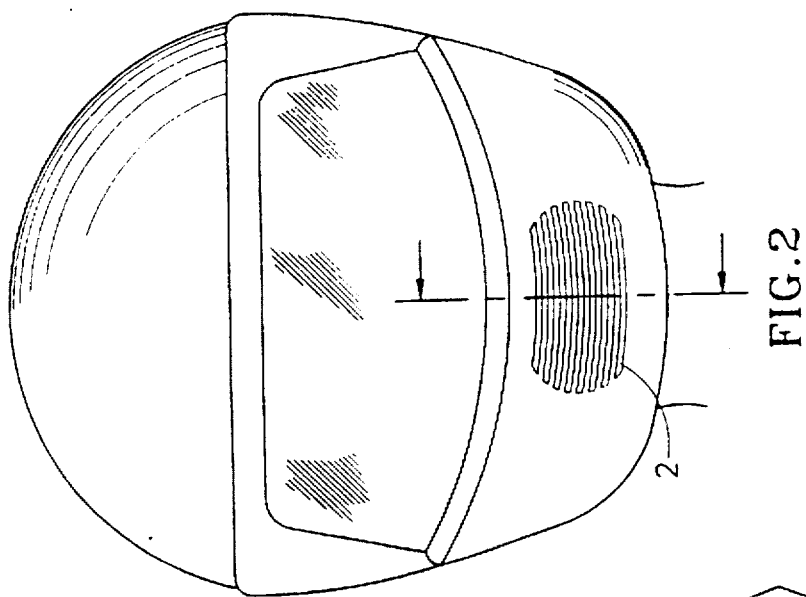
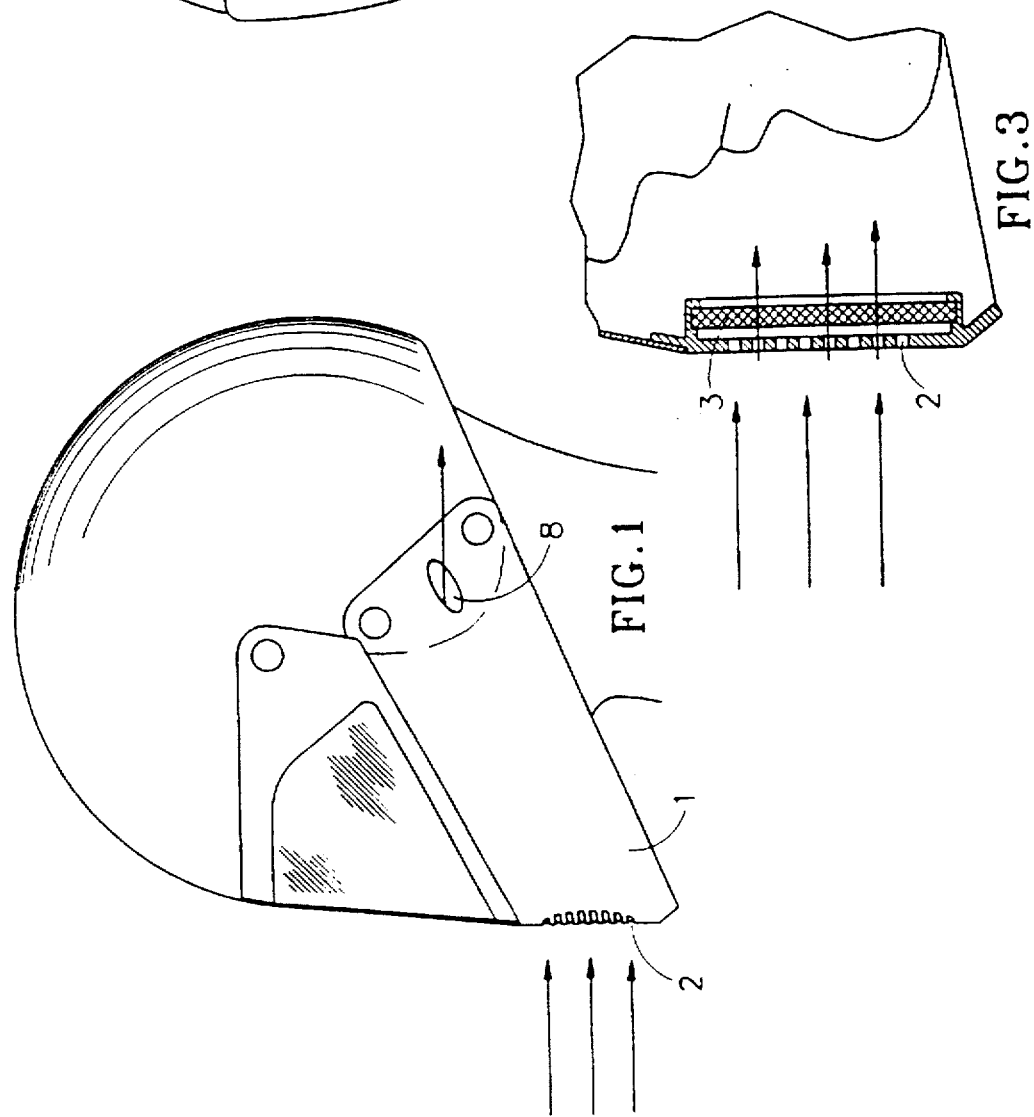

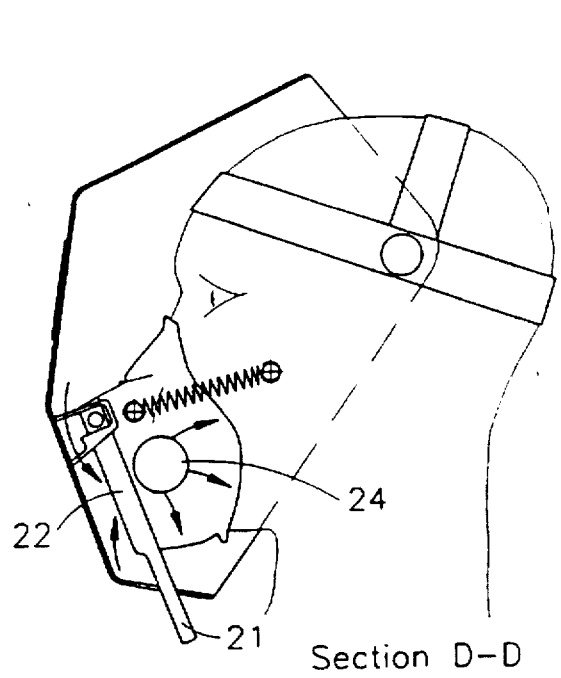
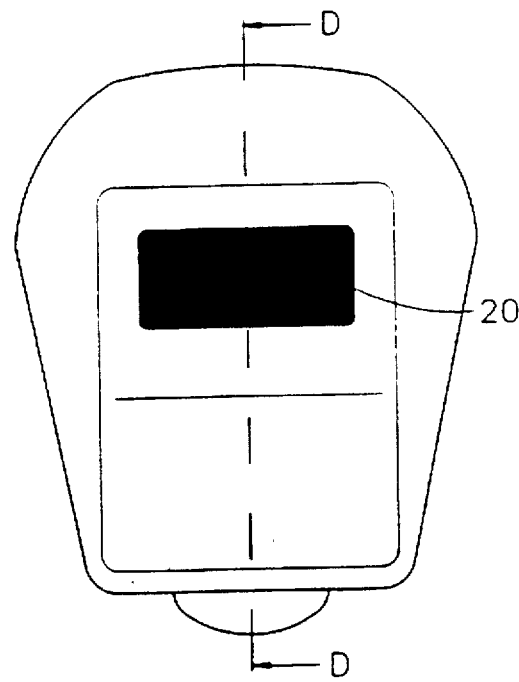
FIG.12　　　　　　FIG.11
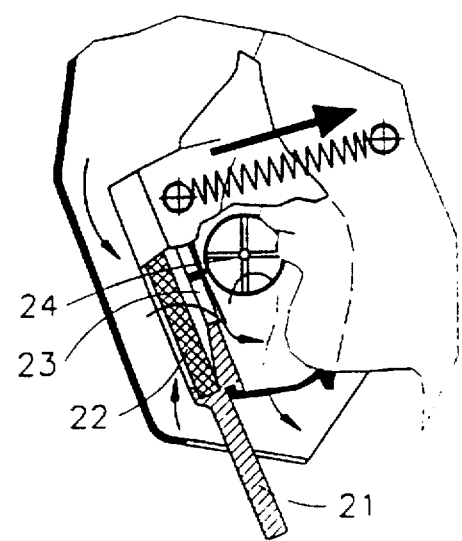
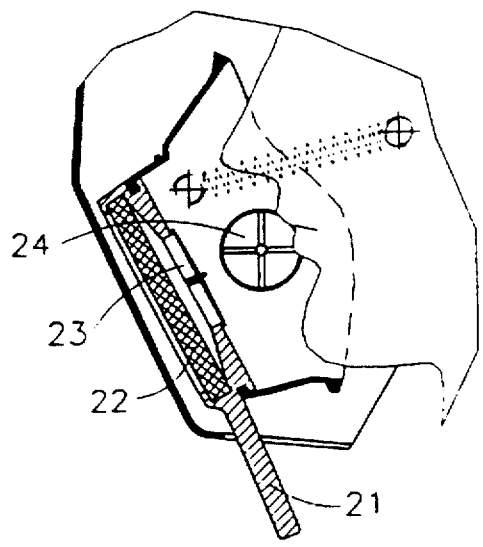
FIG.13　　　　　　FIG.14

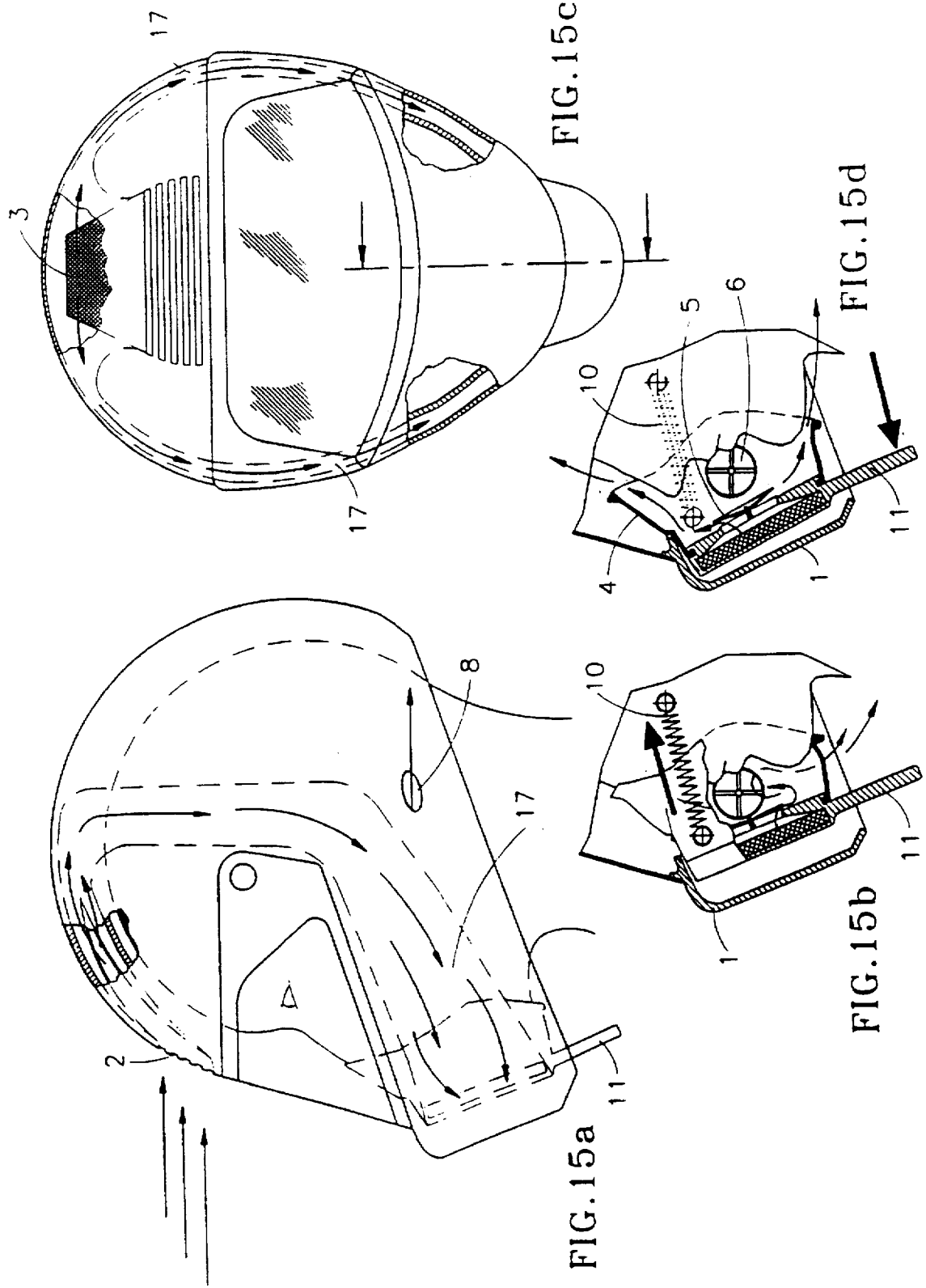

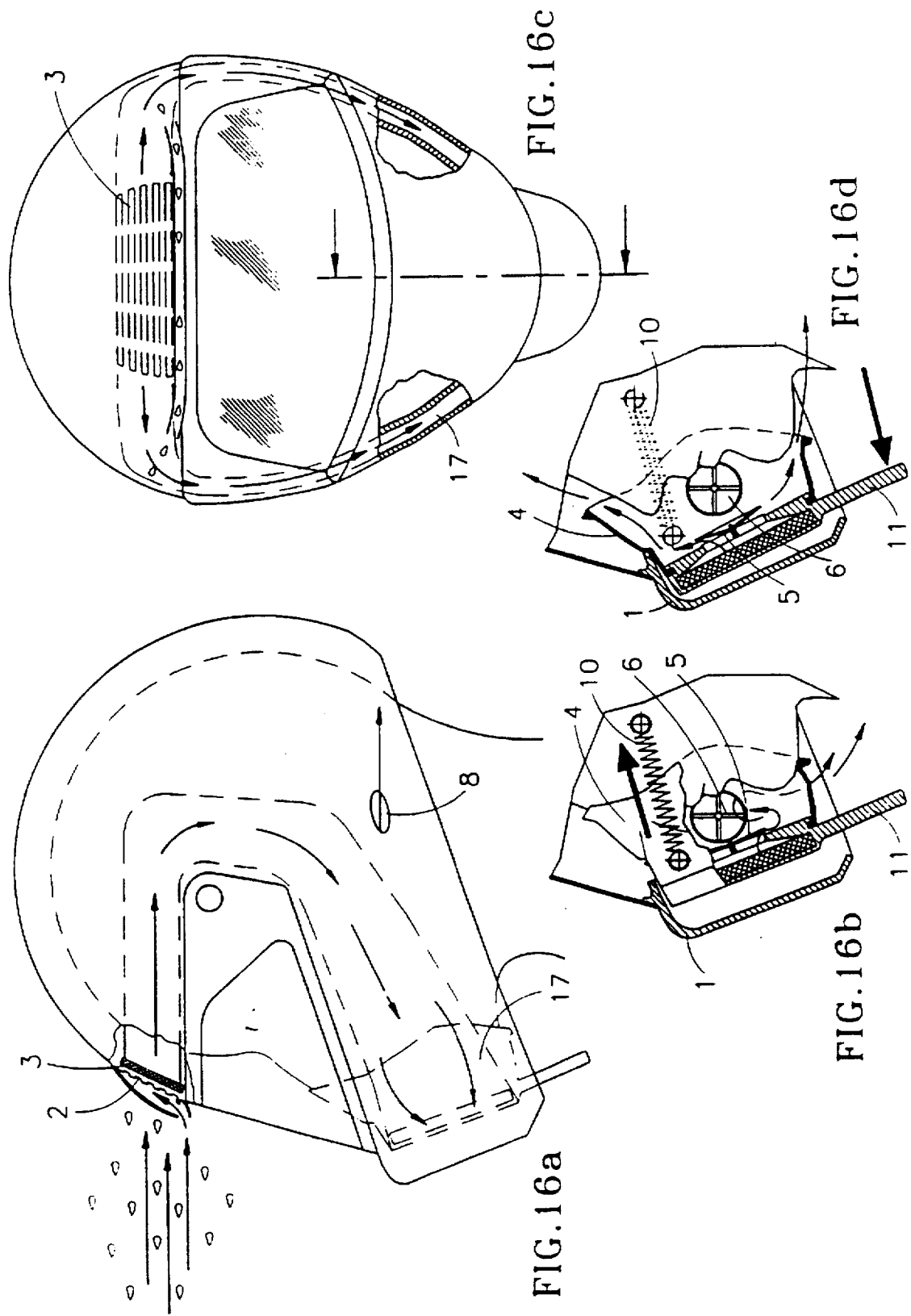

COMBINATION OF A HELMET AND A RESPIRATROR AND A METHOD FOR USING IT

This application is a continuation, of application Ser. No. 08/397,127, filed Apr. 26, 1995.

This invention relates to a combination of a helmet and a respirator.

Nowadays, traffic jams car be a problem, especially in population centers. The air entering roofed automobiles is purified by passing it through fresh air filters whereas people using roofless automobiles, motor cycles, mopeds and bicycles are exposed to airborne impurities. They can, however, resort to using non-integrated, separate respirators. The problems with non-integrated respirators are that they are not comfortable, the impediment to breathing caused by them can be considerable, and the respirator easily becomes wet. Respirators are difficult to get to work both when the wearer is in motion and even when not in motion. Moreover, the helmet's safety construction is impaired because, the respirator is not integrated with the safety helmet. One purpose of the invention is to come up with such a respirator aimed at the aforementioned vehicle users as will not cause essential losses in the properties of safety helmet. When under the influence of the slipstream of air caused by motion and when at standstill (at traffic lights), the respirator worn by the vehicle user must work so that the wearer does not have to breathe in exhaust fumes and dust.

The other purpose of the invention is to come up with a combination of different safety helmets and respirators such as an integrated welder's helmet and/or mask, military helmet, and a construction worker's safety helmet. Respirators integrated with chin guards have not been employed in the said helmet types. In cases where air has been purified prior to being inhaled, it has taken place in a separate purification device from which the purified air has then been led into the respirator. Welders and foundry workers are exposed to a variety of harmful gases. It is, difficult to protect oneself from smoke non-integrated respirators. Masks, on the one hand, and respirators, on the other hand, are generally used as alternatives—not simultaneously. Simultaneous use may lead to a situation in which the respirator cannot be brought firmly enough against the face. Since the respirator and the helmet and/or the mask are separate devices, they are difficult to use and for this reason work safety instructions are neglected.

Currently there are various ways of attaching a respirator to a helmet so that the respirator adapts keenly to the contours of the wearer's face. Another popular solution is to have the inhalation air filtered outside the helmet with hoses being linked to the helmet via which the purified air is then led in to be inhaled. Generally, this air is pumped into the hoses under a certain pressure.

A helmet without a chin protective arch is referred to by the name of half helmet while a helmet with a chin arch is called a full helmet. When a half helmet is provided with a respirator, the end result is not good from the standpoint of safety because it does not provide simultaneous protection for both the chin and the face. Since a respirator mounted in a half helmet has to be attached firmly against the face of the wearer in order to minimize leakages, it may be uncomfortable to the wearer. Considering the lengthy periods that a respirator often needs to be worn, it may cause sensations of sweatiness and uneasiness. Currently, a person wishing to breathe filtered air is forced to select a half helmet instead of a full helmet at the cost of reduced safety.

The solution in accordance with the invention brings about a marked improvement with respect to the aforementioned shortcomings. In the embodiment of this, the solution in accordance with the invention is characterised by what is presented in claims 1 and 9, respectively.

A significant advantage of the invention may he seen in the aspect that the respirator as a whole has been made an integral part of the helmet. The functioning of the respirator can be regulated according to whether the wear is in motion or at standstill. The said respirator can be worn even for lengthy periods of time without discomfort as the sealing part of the face element does not exert pressure upon the face nor does it restrict mouth or facial movements.

The following is a detailed description of the invention with references being made to the appended drawing.

FIG. 1 shows a side view of embodiment of the respirator and helmet.

FIG. 2 shows a front, view of the helmet in FIG. 1.

FIG. 3 shows the section A—A in FIG. 2.

Figure 10C:
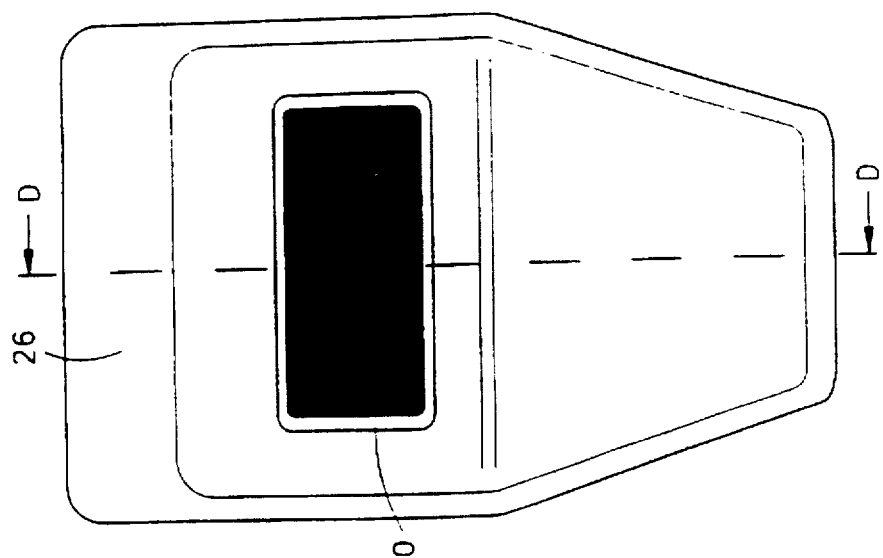
Figure 10B:
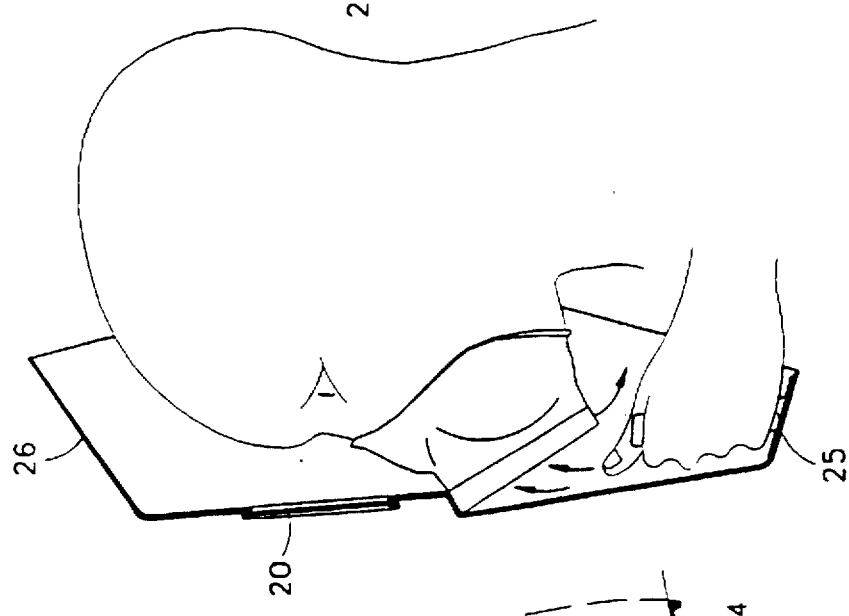
Figure 10A:
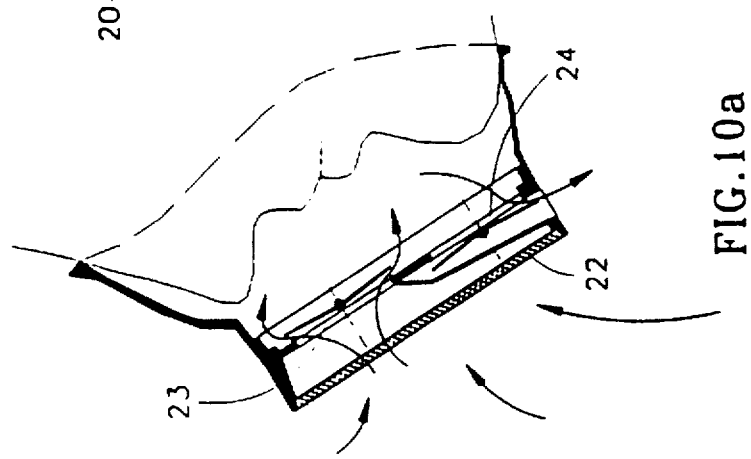

FIG. 10a, b,c shows a welder's =ask with a respirator mounted onto it.

FIG. 11 shows a front view of the welder's mask.

FIG. 12 shows a sectional view of the mask along D—D as shown in FIG. 11. FIGS. 13 and 14 show the mask with the face sealing element in different positions.

FIG. 15 a–d shows a solution connected to the upper part of the visor.

FIG. 16 a–d shows another embodiment of FIG. 15.

FIG. 1 shows a respirator which is mounted onto the chin arch 1 of a helmet, air intake apertures 2 having been disposed into the front part of the said arch. Advantageously, these apertures have been executed as horizontal, elongated perforations as shown in FIG. 2. FIG. 3 shows one embodiment at its simplest. The filter has been placed over supporting ribbing behind air intake apertures 2. The air is guided via the air intake apertures 2 and the filter 3 to the front of the wearer's mouth and nose. Air to be removed is guided out via, for examples the apertures 8 are disposed onto the sides of the chin arch 1.

Figure 4:
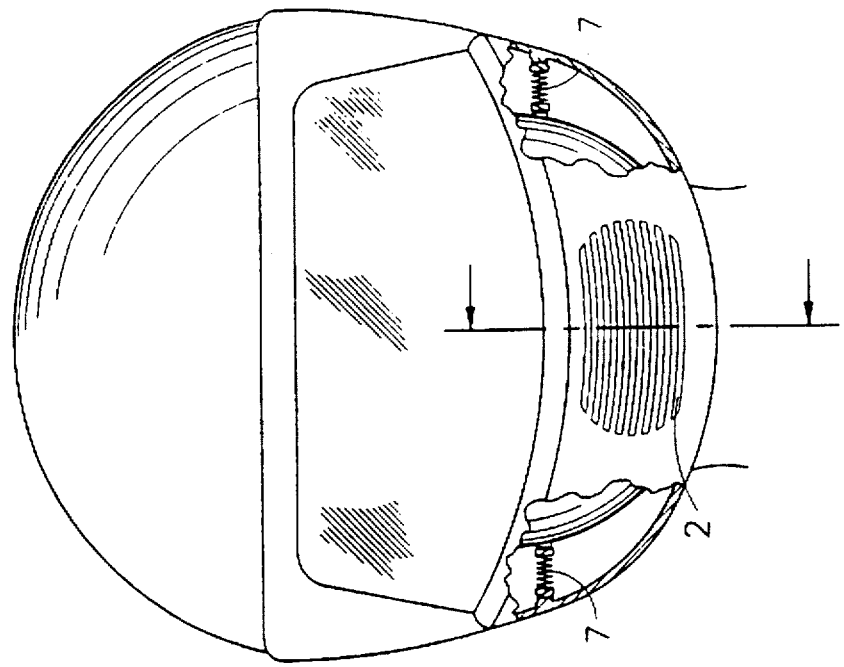
FIG. 4 shows the embodiment shown in FIG. 1 with the addition of the face sealing element from the front with a partial sectional view.
Figure 5:
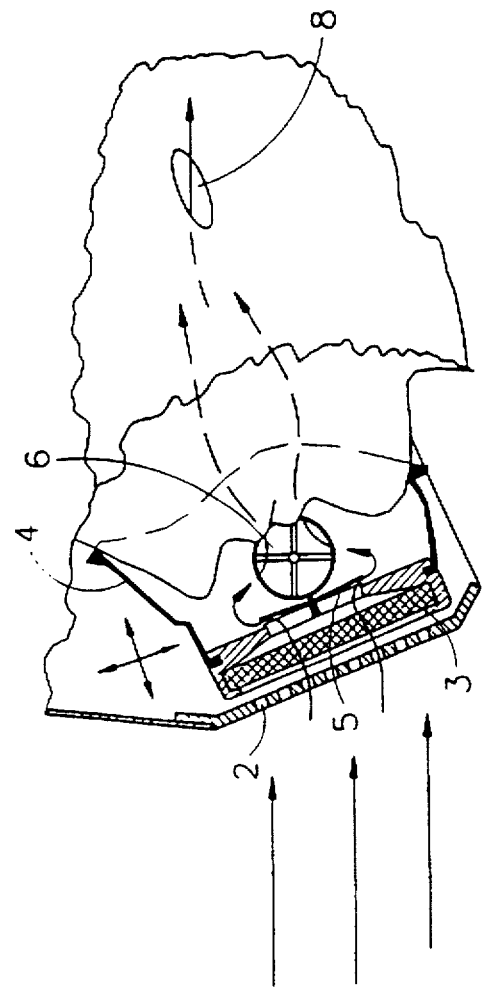
FIG. 5 shows a partial sectional view along B—B in FIG. 4.
Figure 6:
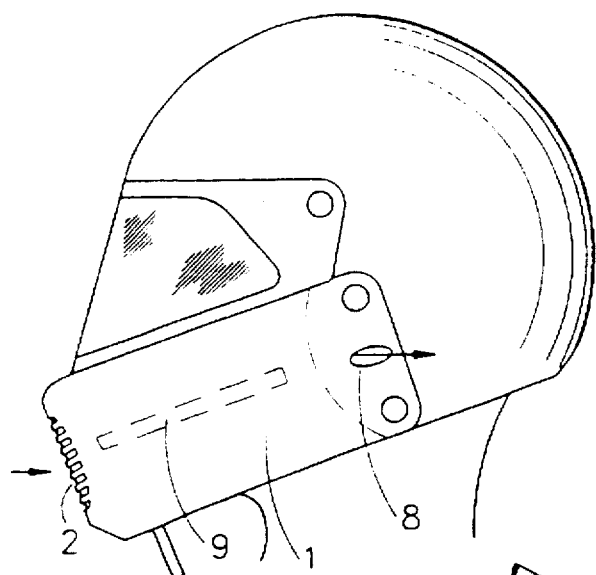
FIG. 6 shows a side view of one embodiment of the helmet and respirator combination.
Figure 7:
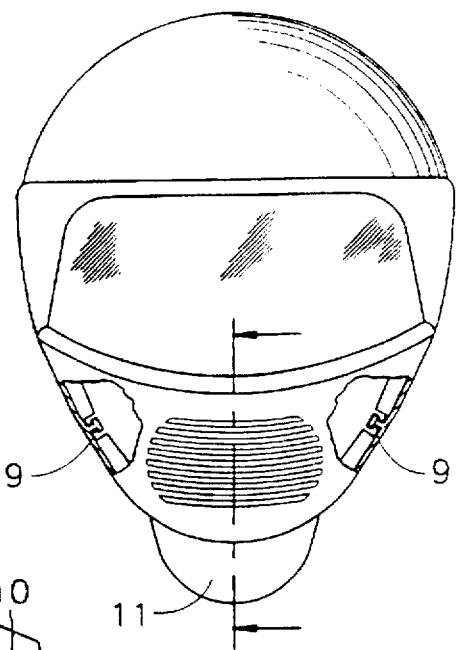
FIG. 7 shows a front view of the combination shown in FIG. 6.

FIGS. 4 and 5 show a situation in which an against-the-face-sealing face element 4, inhalation and exhalation valves 5 and 6, and a flexible respirator fastening mechanism 7 (which may consist of springs that bring the face element against the wearer's face) have been added onto the respirator. The air is guided from the air-guiding apertures 2 to the filter 3 and through it on to the inhalation valve 5 and then to the face element 4. Air that has passed through the exhalation valve 6 is guided out through the apertures 8, for instance, along the sides of the helmet. Continuous arrows are used to indicate the inhalation air and dashed arrows indicate air that is removed from the respirator through the apertures 8. The exhalation valve(s) 6 can be located on one or both sides of the face element.

When this method is employed the air is forced through the filter 3 by ram pressure. The slipstream of air (i.e. ram pressure) produced as motorists, motor cyclists, cyclists, etc., move along forces air through the filter 3 and at the same time purifies the air brought to be in front of the wearer's respiratory organs without there being need for the person to actually draw in air (as there is no resistance). Because ram pressure brings in a surplus of air, part of the air flows out via the exhalation valve, taking along the exhalation air and part of the purified air.

FIGS. 6–9 show yet another more advantageous solution. The functioning of a respirator based on ram pressure can be further improved. FIGS. 6–9 show a solution in which a lever 11 has been included in the combination shown in FIG. 1 and FIGS. 4–5, the said lever being located in the lower part of chin arch 1 in the manner of an extended part. When the user presses this towards him/herself, the respirator moves forwards from the upper part of the chin arch 1 and thereby causes the respirator's face element 4 to be removed from being in contact with the user's face. As more air is forced through the filter 3 at high speed than the user needs for breathing, the surplus air can in this case be guided away through the gap between the face element 4 and the face and then out of the helmet along with the exhaled air. Naturally, the lever 11 must be manufactured from such a material as will not injure the user of the helmet; e.g. stiff rubber type of material.

Figure 8:
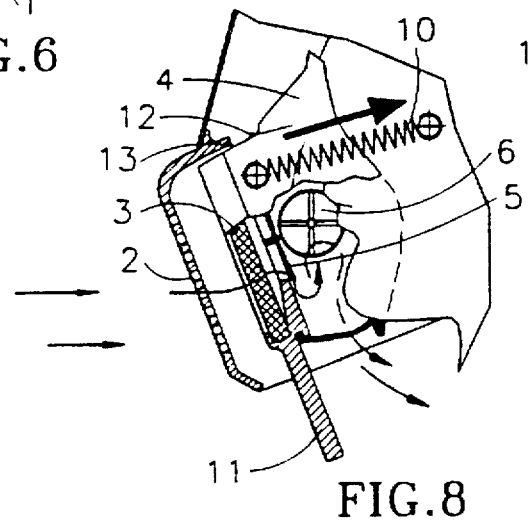
FIG. 8 shows the section along C—C in FIG. 7.
Figure 9:
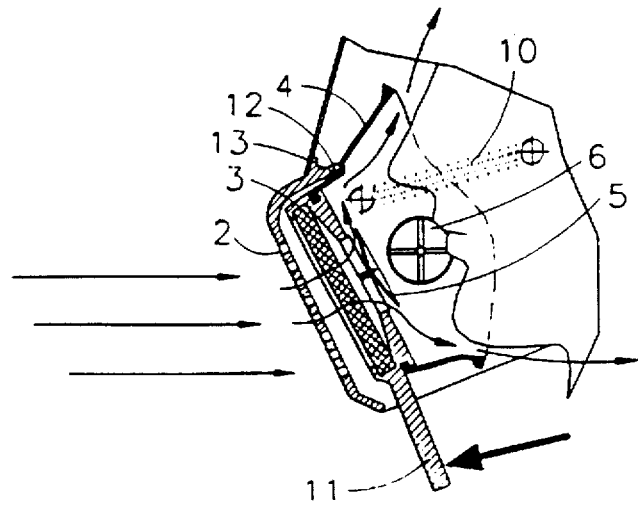
FIG. 9 shows the section in FIG. 7 in another position.

FIG. 8 shows the respirator's slide rail 9 along which the respirator can be moved with respect to the chin arch 1. Since the chin arch 1 includes a vacant, free space that enables the respirator to be moved forward and the face element to be removed from being in contact with the face. A notch 12 has been disposed in the respirator so that in its other extreme position it attaches to the notch 13 in the chin arch so that the face element remains in place. The arrow in bold in FIG. 9 indicates the direction in which the respirator has been moved with respect to FIG. 8. The spring 10 attached to the helmet brings the respirator and/or face element 4 firmly against the user's face.

The evacuation of exhaled air from a respirator that functions under ram pressure can be arranged to take place via evacuation on channels the one end of each channel being on the sides of the helmet and the other end in contact with the exhaled (used) air. The outside air compressed against the sides of the helmet causes an increase in the velocity of the air stream and thereby produces an underpressure in the evacuation channels.

FIG. 11 a, b, c shows a protective mask to which a respirator has been attached. The air to be inhaled can be directed onto a filter directly via apertures made into the front of the mask. When this is done, the functioning of the filter may be quickly impaired because welding gases and other such products rise upwards and become guided directly to the filter. This is why FIGS. 11 a, b, and c are included to show a solution in which the air is guided into the mask to filter 22, not via the apertures made into the front part of the plate, but instead via the rear of the mask. The normal inhalation and exhalation valves 23 and 24 are at the rear of the filter 22. The flow of air is indicated by arrows. The mask extends to below the chin and thus handle 25 can be located inside the mask to enable it to be moved and positioned.

FIG. 11 shows a front view of one embodiment of the mask. Reference number 20 indicates the protective glass. FIGS. 11–14 show an embodiment in which the filter has been placed behind the mask so that the air reaching the filter is directed from behind the mask onto the filter 22 when the user has the mask in the welding position. The lever 21 can be used to bring the respirator firmly against the face or remove it from the face as is described in the above.

It is also possible for air purified elsewhere in the helmet to be led to the protective arch as presented in FIGS. 15 and 16. Since the slipstream is quite powerful at the top of the visor (i.e. the forehead part), air intake apertures 2 can be executed into the helmet above the visor. The air is then immediately guided via the said apertures to a filter 3 located behind them, the said filter being advantageously socklike and with its lengthwise side open in the case of FIG. 15. The opening may advantageously be such that it becomes narrower in the direction of the sock and it may have supporting ribbing at set intervals to prevent loss of strength on the part of the helmet. The purified air is directed via clean air channels 17 located on either side of the helmet's visor to the respirator's face element 4. As before, the face element 4 is provided with inhalation and exhalation valves 5, 6 for air that is breathed in and out. The clean air channel 17 terminates in an optional inhalation valve 5. The face element 4 can be moved as described in the above.

Although it is stated in the above that a socklike filter is used, it can be replaced with filter 3 that is placed in front of the face element 4 as described in the above. When this is done, the air to be purified is led along the air channels 17 on either side of the visor to filter 3 through which the air is led to the exhalation valve 5. Exhaled air is led to the exhalation valve 6. In both cases, the helmet can be made to include simultaneously both the apertures 2 above the visor and the apertures 2 in the chin arch. The shape of the apertures above the visor can be such as are shown in FIGS. 1–3 simultaneously separating the water from the air to be breathed in, if it is raining.

The protective arch can be fixed onto the helmet either permanently or by means of different locking mechanisms. The face element of the respirator car, for instance, be removed loose from the face to from a gap between the face and face element by moving the protective arch at the same time.

It should be noted that, in the above, the invention has been described with reference being made to only one of its; advantageous application examples Different solutions are available for the purpose of moving the respirator. In no way is this intended to restrict the invention to apply only to this example. Instead, numerous variations are possible within the framework of the inventive idea as defined by the following patent claims.

I claim:

1. An assembly for protecting a use's head comprising a helmet and a respirator for purifying of the air to be breathed by the user, said helmet comprising:

a wall structure having a front opening for forward viewing by a user's face;

a shield covering said opening;

an protective arch engaging said wall structure; and an air inlet openings disposed in said helmet through which air passes through, said respirator being joined to said arch, said respirator comprising:

a filter situated between said air inlet and a user's face;

inhalation valve between said filter and said user's face;

a face element movable from a first position in which it is in contact with the face of a user and a second position in which it is not in contact from the user's face; and an exhalation valve located adjacent said face element.

2. The helmet as claimed in claim 1 wherein said face element is movable in relation to said arch.

3. The helmet as claimed in claim 2 wherein air inlet openings for the respirator are disposed into said arch.

4. The helmet as claimed in claim 2 further comprising a visor and wherein said air inlet openings for the respirator are positioned above the visor.

5. The helmet as claimed in claim 3 wherein said filter is located in said arch.

6. The helmet as claimed in claim 3 further comprising a visor and wherein said filter is positioned above the visor.

7. The helmet as claimed in claim 5 further comprising a lever for adjusting the position of the face element with respect to the user's face.

8. The helmet as claimed in claim 7 wherein said air inlet openings are located in the front part of the protective arch.

9. The helmet as claimed in claim 7 further comprising a visor air guiding channels and wherein said air inlet openings are located above the visor whereby air is guided via said air channels to the front of the user's face or the face element.

10. The helmet as claimed in claim 8 wherein said arch is fixed.

11. The helmet as claimed in claim 8 wherein said arch is removable.

12. A method for purifying air through a helmet by a respirator situated therein, said helmet having a wall structure with a front opening for forward viewing by a user's face, a shield covering said opening, a protective arch engaging said wall structure, and an air inlet openings disposed in said helmet through which air passes through, said respirator being joined to said arch, said respirator comprising a filter situated between said air inlet and a user's face, an inhalation valve between said filter and said user's face, a face element movable from a first position in which it is in contact with the face of a user and a second position in which it is not in contact from the user's face, and an exhalation valve located adjacent said face element, said method comprising the steps of:

forwarding said outside air through said helmet via said air inlet, guiding and filtering said air through the filter for purifying said air before the user breaths the same, regulating the flow of air to the face element by moving the face element of the respirator between the position in which the face element is in contact with the user's face and the position in which the face element is not in contact with the face.

13. The method as claimed in claim 12 further comprising the steps of:

evacuating the exhaled air from the respirator which functions on the basis of ram pressure via evacuation channels, the other ends of said channels being positioned along the sides of the helmet where the compressed air causes an increase in the velocity of the air stream and thereby generating an underpressure to the evacuation channels.

14. The method as claimed in claim 13 further comprising the step of:

directing ar entering the respirator via a filter toward a face element onto which part of the respirator the inhalation and exhalation valves have been attached whereupon the face element can be advantageously removed from being in contact with the user's face by means of a lever.

15. The method as claimed in claim 14 further comprising the step of:

moving the face element relative to the arch.

16. An assembly comprising a mask for protecting a user's head and a respirator for purifying the air to be breathed by the user, the mask comprising:

a wall structure having a front opening for forward viewing by a user's face;

a shield covering said opening; and an protective arch engaging said wall structure;

said respirator comprising:

a filter situated between said mask and said user's face;

inhalation and exhalation valves located at the rear of said filter;

a face element movable from a first position in which it is in contact with the face of a user and a second position in which it is not in contact from the user's face.

17. The assembly as claimed in claim 16 further comprising means for taking in air from behind the protective mask.

18. The assembly as claimed in claim 17 further comprising a visor and wherein said filter is positioned above the visor.

* * * * *